United States Patent [19]

Nishio

[11] 4,279,974
[45] Jul. 21, 1981

[54] SOLID ELECTROLYTIC MATERIAL AND USE THEREOF

[75] Inventor: Shinji Nishio, Nagoya, Japan

[73] Assignee: NGK Spark Plug Co., Ltd., Nagoya, Japan

[21] Appl. No.: 131,721

[22] Filed: Mar. 19, 1980

Related U.S. Application Data

[62] Division of Ser. No. 939,109, Sep. 1, 1978, abandoned.

[30] Foreign Application Priority Data

Sep. 2, 1977 [JP] Japan ................................ 52/106193
Jan. 26, 1978 [JP] Japan .................................. 53/6745
Feb. 23, 1978 [JP] Japan ................................ 53/19029

[51] Int. Cl.³ ............................................. H01M 4/36
[52] U.S. Cl. .................................. 429/104; 429/140; 429/193
[58] Field of Search .............. 429/104, 191, 193, 140, 429/247, 149

[56] References Cited

U.S. PATENT DOCUMENTS

| | | | |
|---|---|---|---|
| 3,647,542 | 3/1972 | Berger | 429/40 X |
| 3,661,644 | 5/1972 | Airance | 429/229 |
| 4,082,826 | 4/1978 | Iijima | 429/193 X |
| 4,084,042 | 4/1978 | Ludwig | 429/104 |
| 4,117,208 | 9/1978 | Ludwig | 429/104 |
| 4,137,376 | 1/1979 | Clegg et al. | 429/104 |

*Primary Examiner*—Charles F. LeFevour
*Attorney, Agent, or Firm*—Sughrue, Rothwell, Mion, Zinn and Macpeak

[57] ABSTRACT

The present invention will provide storage batteries, which may be solid electrolytic batteries, and an ionically conductive crystalline solid separator useful in electrical devices. The present invention is characterized by the use of partitioning membranes formed in a honeycomb structure of a plurality of unit tubes arranged in close configuration, the cross-sectional shape of the unit tubes being polygonal. In one preferred embodiment, oxygen transmissive electrodes are provided to yield an oxygen pump.

9 Claims, 20 Drawing Figures

SOLID ELECTROLYTIC MATERIAL AND USE THEREOF

This is a Division of application Ser. No. 939,109, filed Sept. 1, 1978 now abandoned.

BACKGROUND OF THE INVENTION

1. Field of the Invention

This invention relates to a solid electrolyte storage battery or an oxygen pump. More specifically, it relates to a sodium-sulfur storage battery made of $\beta$-$Al_2O_3$ having a large storage capacity per unit weight, a cationically conductive crystalline solid separator used as a diaphragm between a cathode cell and an anode cell in an apparatus for electrolyzing molten sodium chloride to produce chlorine and sodium hydroxide, and to an oxygen ion-conductive crystalline solid separator based on stabilized zirconia.

2. Description of the Prior Art

In the applications described above, reaction is induced with good efficiency by using a number of thin, bottomed hollow cylindrical structures or plates of $\beta$-alumina or stabilized zirconia arranged in parallel as a solid separator. In order to reduce the electric resistance of such a separator, the hollow cylindrical structures or plates must be reduced in thickness and increased in number. However, there is a practical limit to the reduction of the electric resistance of such a separator and increasing the surface area thereof by reducing the hollow cylindrical structures or plates in thickness and increasing them in number.

$\beta$-alumina and stabilized zirconia as are used in the above-described applications are brittle, not only when they are green but also when been converted to sintered bodies. The production of bottomed hollow cylindrical structures or plates having a small thickness from these materials, therefore, is subject to the disadvantages that yield decreases in each step of molding, drying, firing, transportation and assembling, and handling structures thereof requires great care in order to prevent breakage.

For example, in the case of a solid electrolyte battery having a separator composed of an oxygen ion-conductive solid sintered electrolyte, and an oxygen pump made by applying to such a battery a voltage exceeding its open circuit voltage, the solid electrolyte separator usually operates at a high temperature, and generally a high temperature fuel cell (concentration cell) or a direct power generating device is obtained by permeation of oxygen ions through the separator based on partial pressure difference. Phrased differently, a positive potential is generated in areas under high oxygen partial pressure while a negative potential is generated in areas under low oxygen partial pressure. These potentials can be taken out by means of electrodes. Known materials for such separators are of the stabilized zirconia-type, thoria-type, ceria-type, bismuth oxide-type, ceria-lanthania-type, and ceria-thoria-lanthania-type.

The greatest difficulty with such solid electrolyte separators is that their electric conductivity is considerably lower than that of the corresponding molten salt. For this reason, when it is desired to obtain a current of 200 mA/cm² by adjusting the thickness of the electrolyte separator to 1 mm, a separator resistance loss of, for example, 0.2 to 0.8 V is generated. Since the open circuit voltage of one fuel cell is about 1 V, this loss affects the feasibility of the cell. It has been desired, therefore, to develop a solid electrolyte having a higher electric conductivity, and to thin the solid electrolyte itself.

Known solid electrolytes are generally solid solutions. Accordingly, in view of their manufacturing difficulty and handling safety, the thickness of such solid electrolytes in conventional shapes such as a plate, hollow cylinder or tubing shape, used for safety purposes, is generally about 1 to 1.3 mm. A small circular plate having a thickness of 0.5 has been suggested, but building a commercial-scale cell from such small circular plates is complicated, and their handling requires meticulous care. An electrolyte separator having a thickness of as small as 0.1 mm has also been reported, but this can be produced only by flame spraying onto a metal. No single electrolyte structure having such a small thickness has been reported so far.

Even if this electrolyte structures can be obtained from prior art materials, complicated operations and processes must be performed in order to form them to a size for practical applications. With conventional techniques, therefore, it is not easy to obtain both a practical current density and a large total current (i.e., large separator area).

A storage battery or secondary cell having an alkali ion conductive thermally stable separator usually includes a anode reactant consisting essentially of an alkali metal and an cathode reactant consisting essentially of a compound of the alkali metal or an electrolyte containing an alkali metal compound. The separator is preferably a solid electrolyte separator. Alkali ion conductive glass is also known as a separator material.

As is known, the solid electrolytes mentioned above permits the selective passage of, for example, Na ions, when the anode and cathode reactants are in the molten state. By the selective passage of Na ions, the potential difference present between metallic sodium (anode cell) and an electrolyte (cathode cell) capable of reversibly reacting electrochemically with Na, for example, a sulfur-containing electrolyte (sodium sulfide) or a mixture of $AlCl_3$ and $SbCl_3$, which are disposed with a separator therebetween is maintained, thus forming a cell from an electrical output is generated.

A solid electrolyte as separator operates only at the high temperatures at which the metallic sodium and the electrolyte mentioned above are in the molten state. For the purpose of maintenance, cells which operate at lower temperatures have been desired. One example thereof is represented by the cell reaction which takes place in accordance with formula (A) below in the cathode cell, and formula (B) in the anode cell:

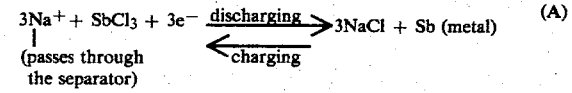
(passes through the separator)  (A)

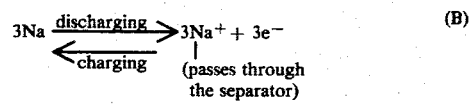
(passes through the separator)  (B)

The cathode electrolyte (mixed salt) used in the above cell reaction has a low melting point, and can function at a lower temperature (200° C.) than the temperature (at least 300° C.) at which a conventional Na/S cell can operate. This is favorable for the corrosion resistance of the material forming the cell. Despite this advantage, this type of cell has the inherent defect that the solid electrolyte has a high electric resistance at lower temperatures, and, consequently, the voltage consumed inside the cell increases and the current generated for use decreases.

A limit on the dimensions of conventional alkali ion conductive solid electrolytes, such as β-alumina, is generally imposed from the standpoint of production and handling thereof, and requires the use of a bottomed hollow cylindrical structure having a thickness of about 0.9 to 1.3 mm and a diameter of 10 to 15 mm. A small circular plate having a thickness of 0.4 mm has been reported, but a large-sized cell cannot be produced from such small circular plates. Moreover, a number of process steps are required to build a cell using such small circular plates as separators. To obtain larger areas, it is necessary to combine still more unit cells and such is difficult in practice.

It has been desired, therefore, to reduce the electrical resistance of solid electrolyte separators by thinning the same.

Furthermore, to obtain a high voltage and high current (high output), it has been greatly desired to simplify and reduce the entire apparatus, increase safety, and to reduce production costs.

SUMMARY OF THE INVENTION

It is an object of this invention to overcome the aforesaid difficulties of the prior art and to provide a thin film of a solid electrolyte and a novel separator structure having a markedly increased separator area in a cell.

The present invention provides an ionically conductive crystalline solid separator which is easy to produce, simple to handle and which is obtained by molding an ionically conductive crystalline sintered body into a unitary structure having a number of passages, termed a honeycomb structure. In spite of the thin mass thereof, such a honeycomb structure is tougher than a hollow cylindrical structure, and comprises many containers or passages as a result of the partitioning thereof by many thin plates.

The toughness of the honeycomb-type solid separator of this invention is ascribable to the fact that it is a unitary structure composed of many cells connected to one another, and these cells reinforce one another to provide sufficient strength, even though their wall thickness is very small.

Since the separator of this invention is of a unitary honeycomb structure, several hundred tubings can be produced at a time by extrusion molding into an integral structure. Furthermore, by using every one or two of such unit tubes as a cathode cell and an anode cell, it is possible to produce at one time a solid separator having an efficiency comparable to several hundred hollow cylindrical separator structures or several tens of thin separator plates.

The honeycomb structure-type separator of this invention consists of unit tubes having any desired sectional shape such as a triangle, tetragon or hexagon which are aligned in juxtaposition.

The invention also provides a novel oxygen pump by applying to a solid electrolyte cell having the above characteristics a voltage exceeding the open circuit voltage of the cell.

When a voltage exceeding the open circuit voltage of the electrolyte cell is applied from the exterior, oxygen ions move from low concentration areas (with low oxygen pressure) to high concentration areas (with a higher oxygen pressure), and act to maintain equilibrium, thereby supplying oxygen.

DETAILED DESCRIPTION OF PREFERRED EMBODIMENTS

Figure 1:
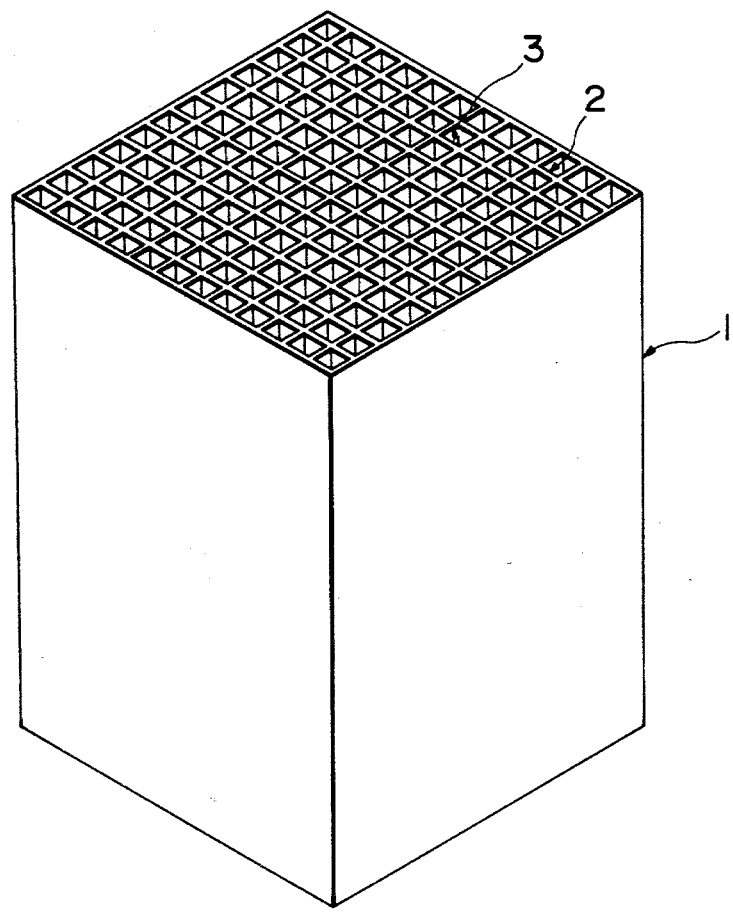
FIG. 1 is a perspective view of one example of the ionically conductive crystalline solid separator of the invention.

FIG. 1 shows an ionically conductive crystalline solid separator 1 of a honeycomb structure with a tetragonal cross section. Reference numeral 2 represents a partitioning wall and 3 a unit tube.

The cross-sectional shape of the unit tube 3 of the honeycomb structure of this invention may be a triangle, tetragon, hexagon, another polygon, any other desired shape, or any combination thereof. Triangular, tetragonal and hexagonal shapes are especially preferred to increase the separator area and for electrode cell arrangement. Generally, the aforesaid polygonal shapes, corrugated forms, such as a sinusoidal curve, and sectional shapes formed by a combination of these are used. It should be noted, however, that these honeycomb sectional shapes are merely illustrative, and the invention is not limited thereto.

Figure 2:
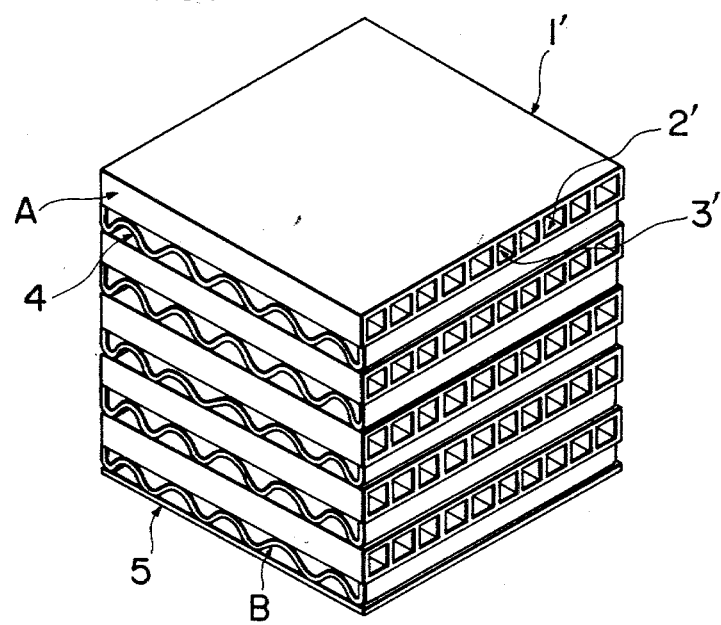
FIG. 2 is a perspective view showing another example of the separator of this invention.

The honeycomb may have a structure in which all unit tubes are aligned parallel as shown in FIG. 1. Or, as shown in FIG. 2, tube rows or layers each consisting of parallel unit tubes may be laminated in a direction crossing each other at right angles. The tube rows in the direction crossing each other at right angles in this honeycomb structure may have the same or different cross-sectional shapes. Such a perpendicularly crossing honeycomb structure has the advantage that it permits easy gas supply and discharge, and easy construction of electrodes, connections and lead lines. An anode cell and a cathode cell may be disposed alternately in this perpendicularly crossing honeycomb structure.

Figure 3:
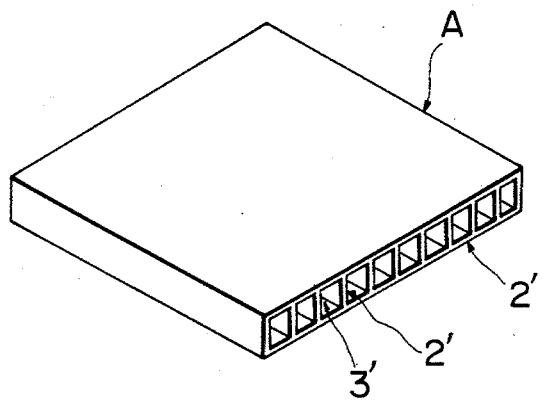
FIG. 3 is a perspective view of a single layer constituting the separator shown in FIG. 2.
Figure 4:
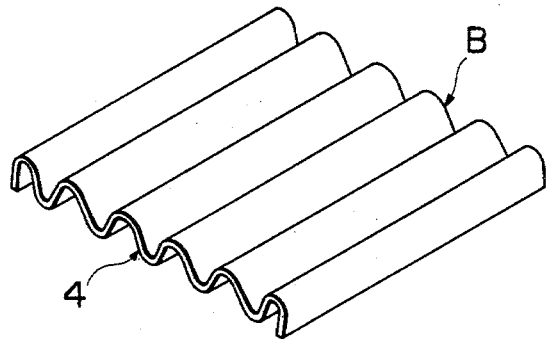
FIG. 4 is a perspective view of a corrugated sheet constituting the separator shown in FIG. 2.

The perpendicularly crossing honeycomb 1' shown in FIG. 2 is constructed by stacking honeycomb single layers A shown in FIG. 3 having a number of tubes 3' provided by partitioning walls 2' in one direction alternately with corrugated sheets B as shown in FIG. 4 having a number of bent portions 4 consisting of sinusoidal curves (in cross section) so that the axial lines of the tubes cross the axial lines of the bent portions at right angles to each other, and then bonding them. The final corrugated sheet B is bonded to a bottom plate 5.

Electrolysis can be continuously performed using a honeycomb structure as shown in FIG. 1 using openings on one side as feed openings for electrolytic solution and openings on the other side as discharge openings for electrolytic solution. Since in this honeycomb structure the tubes are aligned at right angles to each other, even when a catholyte solution or anolyte solution is supplied at a time from each side, no mixing occurs, and the electrolysis can be continued easily. For the viewpoint of fitting electrodes and in other aspects it is easy to build the desired device from this honeycomb structure.

An alkali ion-conductive thermally stable separator prepared by using a $\beta$-alumina type honeycomb structure consists essentially of $\beta$-alumina, preferably $\beta$-alumina containing $\beta''$-alumina.

$\beta$-Alumina denotes a hexagonal crystal expressed by the basic composition $Na_2O.11Al_2O_3$ or $K_2O.11Al_2O_3$ (usually, the content of sodium is somewhat large, and the content of potassium is about 7%), usually its sintered polycrystalline body. A pure $\beta$-alumina sintered body shows about 5 to 20 times as high a resistance as a monocrystal. Products whose resistance has been lowered by addition of $Mg^{++}$, $Ni^{++}$, $Zn^{++}$, $Cu^{++}$, etc. are also available. The $\beta$-alumina, as referred to in the present application, includes all of these varieties. Desirably, the $\beta$-alumina should not contain ingredients which may be detrimental to resistance against corrosion by alkalies, and to ionic conductivity.

A honeycomb consisting essentially of $\beta$-alumina can be produced by the method described in Example 5 to be given hereinbelow. The general method of producing the $\beta$-alumina powder and a solid electrolyte block composed of $\beta$-alumina is described in Japanese Patent Publication No. 66631/72.

The honeycomb used in this invention may be formed from the same $\beta$-alumina powder.

The general method of producing a honeycomb as used in this invention is known, for example, from the specification and drawings of Japanese Patent Publication No. 1232/76, and this method can be used in this invention.

Furthermore, the honeycomb-type separator of this invention consisting essentially of $\beta$-alumina containing $\beta''$-alumina can be produced by the method described in Japanese Patent Application No. 125782/77 filed by the same applicant as the present application. $\beta''$-Alumina-containing $\beta$-alumina exhibits a lower separator resistance, preferably $\beta''$-alumina is included in a range of 55 to 85 wt%, and, therefore, is a most preferred honeycomb-type separator. Specifically, at 300° C., for example, $\beta$-alumina has a volume inherent resistivity of 10 to 20 ohms·cm and improved commercially available varieties of $\beta$-alumina have a volume inherent resistivity of about 10 ohms·cm. In contrast, the $\beta''$-alumina-containing $\beta$-alumina preferably used in this invention has a volume inherent resistivity of about 4 to 8 ohms·cm.

The peak intensity ratio ($I\beta/I\beta''$) of $\beta$-alumina containing $\beta''$-alumina to $\beta''$-alumina preferably used in this invention in a powder X-ray diffraction pattern thereof is in the range of 0.25–1.0, preferably 0.5–0.8. $I\beta$ represents the peak intensity of $\beta$-alumina on the $\alpha=2.69$ Å (017) plane, and $I\beta''$ represents the peak intensity of $\beta''$-alumina on the $\alpha=2.60$ Å (01, 11) plane.

Highly ionically conductive ceramics consisting essentially of such $\beta$-alumina containing $\beta''$-alumina (solid electrolytes) are described in more detail in the specification of Japanese Patent Application No. 57598/76 filed by the same applicant as the present application.

The honeycomb structure of this invention made of the above material can be obtained, for example, with a wall thickness of 0.15 mm and one side of a unit tube measuring 5 mm, or with a wall thickness of 0.4 mm and one side of a unit tube measuring 15 mm. The structure is tough as a result of the unit tubes reinforcing each other, and has a large area per unit volume.

Referring to FIGS. 5 to 8, each unit tube 30 is used either as a cathode cell (+, 6) or a anode cell (−, 7) according to the arrangement of the tubes. The partitioning wall is a set of an adjacent cathode cell 6 and anode cell 7 is formed by a honeycomb diaphragm 20. The anode cell 7 is filled, for example, with metallic sodium, and the cathode cell 6, in which a known cathode is disposed as will be described hereinbelow, is filled with a molten mixed salt of, for example, $AlCl_3$, $NaCl$ and $SbCl_3$. A unit cell 9 formed in this way can be arbitrarily placed in any of the unit tubes 30 of the honeycomb structure.

Figure 5:
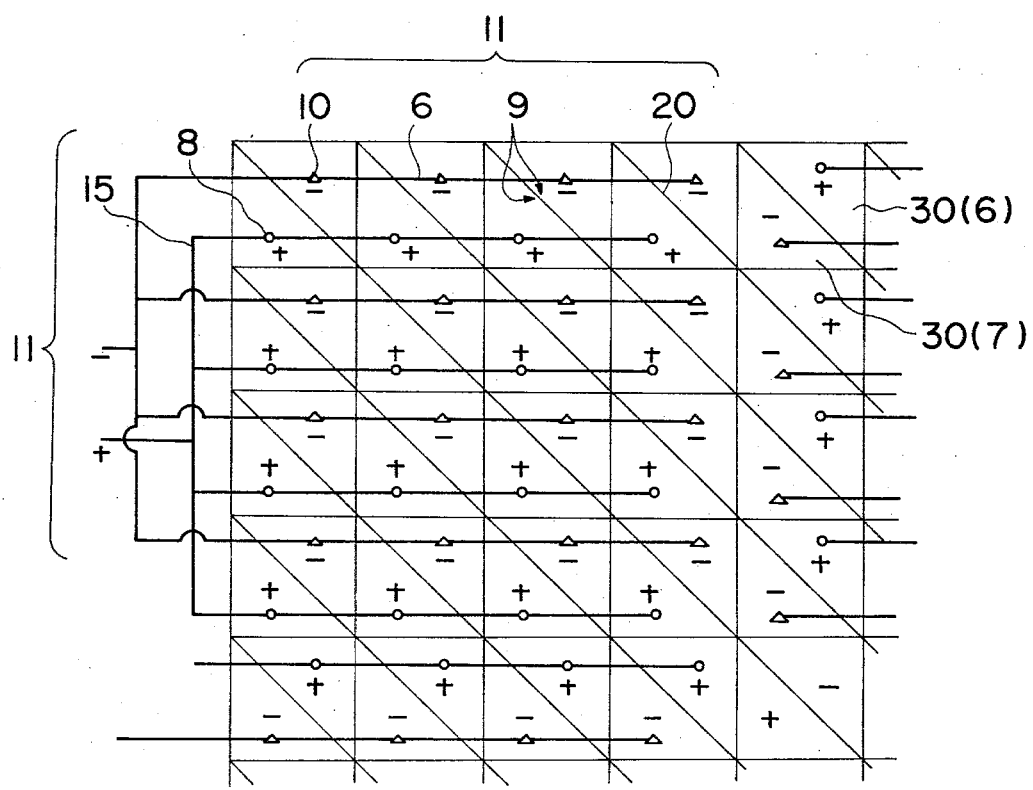
FIG. 5 is a top plan showing one embodiment of a storage battery having a honeycomb structure in accordance with this invention.

Various arrangements can be selected according to the cross-sectional construction of the honeycomb and the required voltage and current density. For example, as shown in FIG. 5, a + cell and a − cell can be alternately arranged in unit tubes 30, each of which has a right-angled triangular cross-sectional shape formed by a lattice-like diaphragm and parallel diaphragm connecting diagonal lines at the crossing points of the lattice. In this arrangement, one + cell and − cell set is disposed in each opening of the lattice structure. In this structure, one + cell, in principle, is contiguous to − cells on three sides thereof. The advantage of this arrangement is that all diaphragms 20 can be effectively used. Many unit cells 9 so formed are arranged such that three unit cells 9 are formed for each unit tube 30 excepting the unit tubes at the outside area (three sides of each tube being diaphragms).

According to particular needs and purposes, these numerous unit cells are connected in series and/or in parallel. In series connection, however, care must be taken so that the electromotive force of one unit cell will not be consumed by the charging of another unit cell.

In one preferred embodiment of the invention as shown in FIG. 5, electrodes (8, 10) of the alternately aligned + cell and − cell are first connected parallel to each other in the transverse direction, and then connected parallel to each other also in the longitudinal direction. This parallel connection can be effected in the entire, or a part of, the honeycomb, and, thus, one integrated cell 11 is formed. The diaphragm at the boundary of the integrated cell may be insulated as desired. When integrated cells 11 are formed partly in the honeycomb, the arrangement of the + and − cells in adjacent integrated cells are reversed so that the diaphragms between the adjacent integrated cells serve merely as partitioning walls (see FIG. 5). The integrated cells so obtained have a definite voltage and a definite current density. By connecting these integrated cells in series and/or in parallel, the desired voltage and current can be obtained.

According to this invention, two or more honeycomb modules may be connected in series in the transverse direction by known means to form a larger honeycomb cell. Teflon rubber is a preferred bonding agent for such honeycomb structures. Sealing glass (for example, a sealing glass consisting mainly of $SiO_2$ and $Na_2O$ having substantially the same coefficient of expansion as $\beta$-alumina) can also be used.

Figures 7, 8:
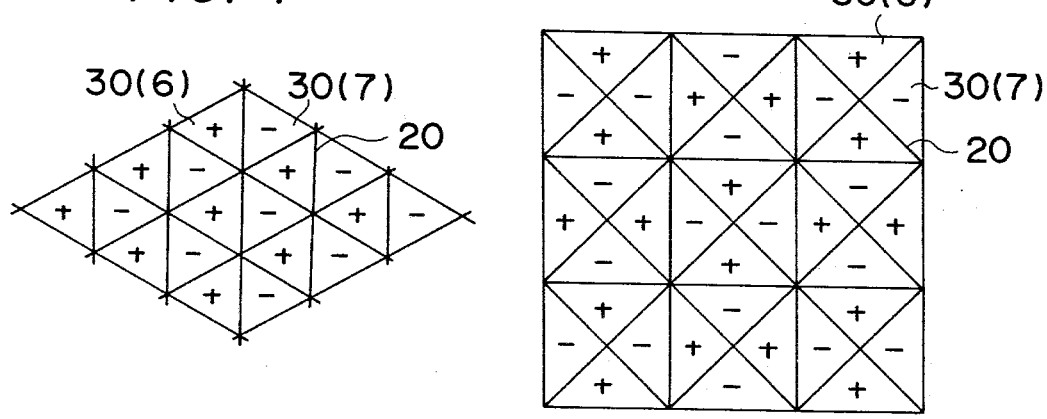
FIG. 7 is a top plan showing still another embodiment of a storage battery having a honeycomb structure in accordance with this invention.
FIG. 8 is a top plan showing yet another embodiment of a storage battery having a honeycomb structure in accordance with this invention.

A honeycomb composed of unit tubes having an equilateral triangular cross-sectional shape as shown in FIG. 7 can also be used (reference numerals have the same meaning as in FIG. 5). The most preferred arrangement of electrode cells in this case is an alternate alignment of + and − cells. In this case, the unit cell connection shown in FIG. 5 can also be used.

Another specific example of unit tubes 2 having a triangular cross-sectional shape is shown in FIG. 8 (reference numerals have the same meaning as in FIG. 5). Each of these honeycomb unit tubes is formed by partitioning with one set of perpendicularly crossing diaphragms which connect opposing apexes of each opening in the lattice structure. In this honeycomb, + and − cells can also be aligned alternately as shown in FIG. 8.

It is further within the scope of this invention to connect to honeycomb unit cells as described above any desired electrode cells other than those specifically illustrated in the accompanying drawings.

Figure 6:
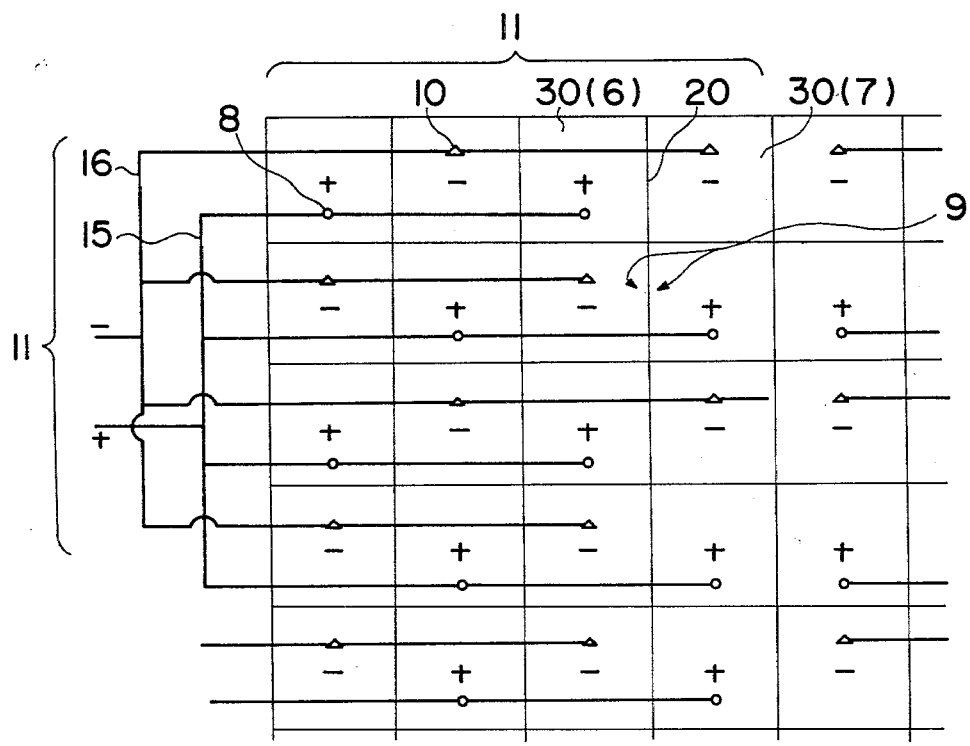
FIG. 6 is a top plan showing another embodiment of a storage battery having a honeycomb structure in accordance with this invention.

A lattice honeycomb composed of unit tubes 30 having a rectangular cross section can also be formed in accordance with this invention. (+) and (−) electrode cells may also be arranged alternately in lattice honeycombs. By connecting the resulting unit cells 9 in parallel as shown in FIG. 6 (reference numerals are the same as in FIG. 5), one integrated cell can be obtained. In adjacent integrated cells, electrode cells of the same polarity are arranged in adjacent unit tubes 30 (in other words, + and − are reversed at the boundary area of the integrated cells) and the diaphragm at the boundary area serves as a partitioning wall for the integrated cells.

The alternate arrangement of + and − electrode cells as described above provides a mode of using diaphragms with optimum efficiency. The present invention, however, allows other modes of arrangement, for example, alternate row arrangement, concentric or radial arrangement in honeycombs composed of radial or concentric diaphragms, and other desired arrangements corresponding to the desired honeycomb shape. Connection of unit cells is properly selected according to the variety of electrode cell arrangement.

The electrodes of the honeycomb cell in accordance with this invention can be formed by known methods. The cathode may be formed, e.g., preferably from a conventional cathode metal such as molybdenum, nickel, tantalum, beryllium, tungsten, cobalt, iron or copper, or an alloy of such a metal (for example, stainless steel). The anode cell is filled with a conventional molten alkali metal, and it is sufficient that the electrode is immersed therein in the form of a rod.

The material for the cathode, though conventional, somewhat varies according to the electrolyte used. For example, when sulfur or sodium polysulfide is used, stainless steel, titanium nitride, graphite or carbon, especially in fibrous or felt form, may be used as a corrosion resistant electrode material. In this case, it is most preferred to use carbon or graphite powder as an auxiliary current collector in conjunction with a fibrous or felt like electrode of the above materials. Basically, the same electrode materials can be used also when a mixed salt of $AlCl_3$, $NaCl$ and $SbCl_3$ is used as an cathode reactant.

To reduce the resistance of contact of the cathode with lead wires, it is beneficial to compression mold a ribbon, wire, net, etc., of stainless steel and graphite felt, and to remove a current via the stainless ribbon, etc. Such electrodes can be fixed by known thermally stable corrosion resistant insulating materials or insulation sealing agents, such as Teflon rubber.

By the aforesaid construction, the resistance inside the cell is due mainly to the resistance of the anode and the diaphragm resistance of $\beta$-alumina, etc., whereby the effects of the invention clearly appear.

In the above embodiments of the present invention, it is beneficial to use a reservoir for each of the cathode and anode reactants, as is known in the art. For the honeycomb type storage batteries of this invention, reservoirs having various conventional supply means can be used according to the respective arrangement of the + and − electrode cells. Thus, it is possible to absorb or alleviate changes in quantity and chemical composition of the reactants at the time of charging and discharging within certain tolerances, and to increase the operating time and output of the storage battery in one cycle.

Furthermore, as is well known, these systems are maintained in an atmosphere of a dried inert gas to prevent oxidation and moisture absorption by the reactants, especially molten alkali metal.

In the honeycomb cell of this invention, each reactant can be fed to each electrode portion within certain limits using a reservoir or a flow-through method. Accordingly, the small cross-sectional area of the honeycomb is not believed a substantial drawback. Furthermore, with a honeycomb storage battery, a drastic decrease in internal resistance and a large diaphragm surface area per unit volume can be obtained. This is a tremendous advance in the art in that the battery can be small while a large current can be obtained therefrom.

It is within the scope of this invention to attach or substitute known techniques including diaphragm materials, electrodes, reactants at both electrodes, lead line connections, sealing agents, sealing gases, and charging and discharging means to or for the present invention in the embodiments of the present invention, or to use known equivalents in these embodiments.

According to this invention, not only are the discharge characteristics but also the charge characteristics of the battery are improved. The features and advantages of the invention will become more apparent from the Examples given hereinbelow.

In the specific working examples of the invention, $\beta$-alumina is used for comparison with known separators. The use of $\beta$-alumina containing $\beta''$-alumina increases the effects observed.

The invention will now be further described with regard to a solid electrolyte cell having a honeycomb structure including an oxygen ion conductive material as a separator.

The separator for a honeycomb structure in accordance with this invention includes separators consisting essentially of at least one member of the group consisting of stabilized zirconia, thoria, ceria.lanthania, ceria.thoria. lanthania, ceria, and bismuth oxide. Stabilized zirconia, as used herein, denotes a solid solution containing zirconia as a main ingredient (>50 mol%) which retains a cubic crystal structure over a broad temperature range. Examples of stabilized zirconia include $(ZrO_2)0.92$ $(Yb_2O_3)0.08$, $(ZrO_2)0.9$ $(Y_2O_3)0.1$, $(ZrO_2)0.85$ $(CaO)0.15$, and a solid solution of $ZrO_2$ and $Nd_2O_3$, $Gd_2O_3$, $La_2O_3$ or $Sc_2O_3$. Thoria includes a solid solution of $ThO_2$ and an oxide of Ca, Mg, Sr, La or Y. Ceria includes a solid solution of $CeO_2$ and an oxide of La or Y. Bismuth oxide includes $(Bi_2O_3)0.8$ $(SrO_2)0.2$. Among these electrolyte solid solutions, stabilized zirconia-type solid solutions are a most preferred embodiment from the viewpoint of economy and practical application. For example, the degree of oxygen ion conductivity which the honeycomb structure containing stabilized zirconia shows is 0.091 mho/cm at 1,000° C.

The smallest practical thickness of the partitioning wall of the honeycomb structure of this invention is about 0.1 mm when no reinforcing agent such as metal is used. For example, honeycomb structures can easily be obtained with a wall thickness of 0.4 mm and a unit tube interior diameter of 15 mm (rectangular cross section) or with a thickness of 0.15 mm and a unit tube inside diameter (same basis) of 5 mm. The exterior wall of the honeycomb module is generally made somewhat thicker. Each of the partitioning walls of the honeycomb is very thin, but they reinforce each other to provide feasible strength and dimension.

According to this invention, any desired partitioning wall of the above honeycomb can be used as a partitioning wall 101. Unit tubes on both sides of the partitioning wall 101 become an anode cell (under high oxygen pressure, 103) or a cathode cell (under low oxygen pressure, 104) (preferably at both ends). This tape-like end portion 110 forms a connection between electrodes and a lead line and, if desired, can be insulated in a conventional manner as when the partitioning wall is very thin, short circuiting between the two electrodes can occur at the end surface of the partitioning wall at the end portion of the honeycomb. Furthermore, it may be difficult to connect the two electrodes separately or take out lead lines but by providing a desired connection or lead line at one or both surfaces of the tape-like end portion 110, or at one or both ends of the honeycomb by conventional methods (usually by baking), one honeycomb module is made which serves as one cell module.

Figure 14:
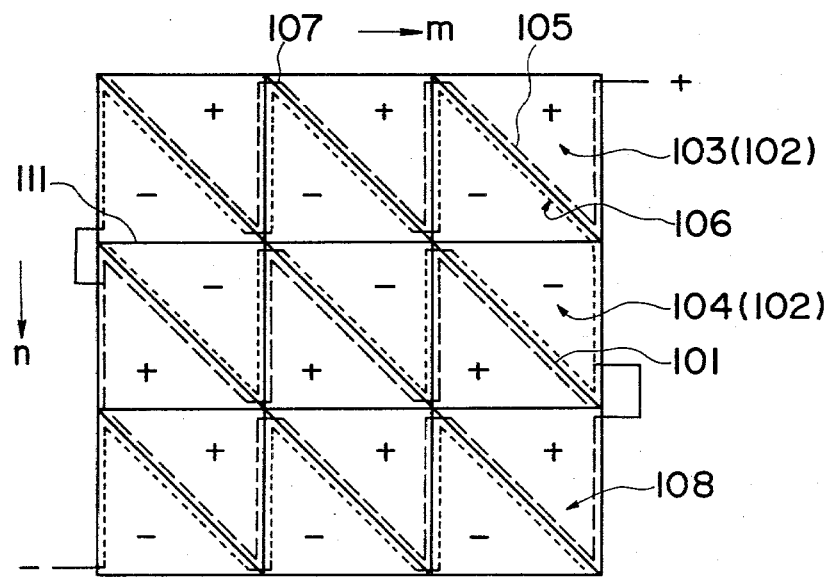
FIG. 14 is a top plan showing still another embodiment of a storage battery of the invention having a honeycomb structure.

One preferred embodiment of an electrode arrangement in accordance with this invention is shown in FIG. 14. In this embodiment, a honeycomb is used which is composed of unit tubes 102 of a triangular cross section which are formed by parallel and orthogonal partitioning walls and parallel partitioning walls connecting the diagonal lines of rectangular units formed by the aforesaid parallel and orthogonal partitioning walls. In the first row of parallel unit tubes 102, (+) cells are disposed, while in the second and third tube rows, (−) cells are disposed. Then, (+) and (−) cells are alternately aligned in parallel tube rows. Electrodes are formed with a serrated shape leaving a tape-like end portion 110 at both end portions of the honeycomb, and a straight partitioning wall 111 is left on the lateral side. Unit cells are formed at the serrated perpendicular portions and inclined portions. In this embodiment, no insulation is required between electrodes (105 and 106) of the unit cells belonging to one unit tube 102, and the electrodes on two diaphragms belonging to the same unit tube may be continuous. When positive and negative electrodes are each connected sideways by connection 107 for each parallel tube row, a current having a magnitude of m $(i_1+i_2)$ A is obtained (wherein $i_1$ and $i_2$ represent the currents of two unit cells belonging to one unit tube, and m is the number of (+) cells in the lateral parallel tube row). The series connected units thus-formed may be connected in parallel or in series to form one honeycomb module cell. For example, if all are connected in series as shown in FIG. 14, an electromotive force neV (where e is the electromotive force of a unit cell and n is the number of series connection, i.e., the number of vertical rows of serrated unit cells) can be obtained.

Thus, between the output terminals of such a honeycomb module cell, a voltage of neV x current m $(i_1+i_2)$ A is obtained as an output. The electromotive force e depends upon diaphragm resistance, electrode resistance, oxygen ion concentrational difference and the temperature of the gas, while $i_1$ and $i_2$ additionally depend upon the available area of the diaphragm. Accordingly, in this embodiment of the invention, n and m can be made large so that sufficiently large currents and voltages for practical application can be obtained. Furthermore, any desired output can be obtained partitioning wall 101 forms a unit cell 108 by having electrodes 105 and 106 on its surface. Unit cell 108 is formed using the partitioning wall between adjacent unit tubes as a diaphragm. In theory, the number of unit cells that can be formed per unit tube corresponds to the number of partitioning walls (the number of sides) which one unit tube has. The number of effective partitioning walls, i.e., the number of unit cells, per unit tube depends mainly on the arrangement of anode and cathode cells, the arrangement of electrodes and the mode of connecting the electrodes.

The partitioning wall-diaphragm 101 of the same unit cell 108, if required, has electrodes on both of its surfaces which are continuous to, or insulated from, adjacent diaphragms. The electrodes should not hamper the passage of oxygen, and are preferably porous and formed by known methods from platinum, nickel, or alloys containing such a metal as a main ingredient (>50 mol%). The electrodes permit effective removal of a potential difference generated on both sides of the diaphragm. It is necessary that the contact resistance between the diaphragm and the electrode be low, and, since the electrode is usually operated at high temperature, it should have thermal stability and oxidation resistance.

Figure 11:
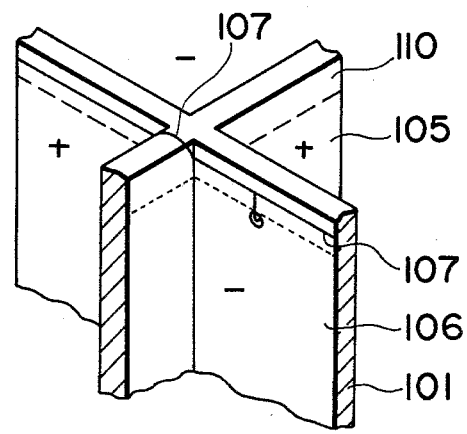
FIG. 11 is an enlarged perspective view of a part of the honeycomb structure shown in FIG. 10.

This embodiment wherein a surface electrode on diaphragm is involved is as shown in FIG. 11, i.e., a tape-like portion remains on the partitioning wall at an end portion of the honeycomb (at least one end), and by connecting these module cells in series or in parallel to each other. It is also possible to enlarge or extend the modules in accordance with this invention by soldering with, for example, 18% Ni/82% Au alloy.

Figure 10:
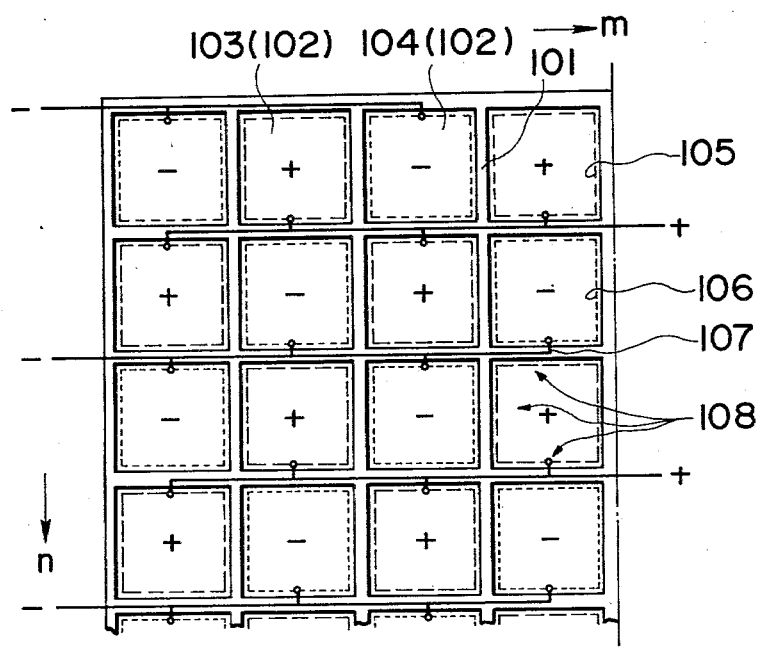
FIG. 10 is a top plan showing a further embodiment of a storage battery of the invention having a honeycomb structure.
Figure 12:
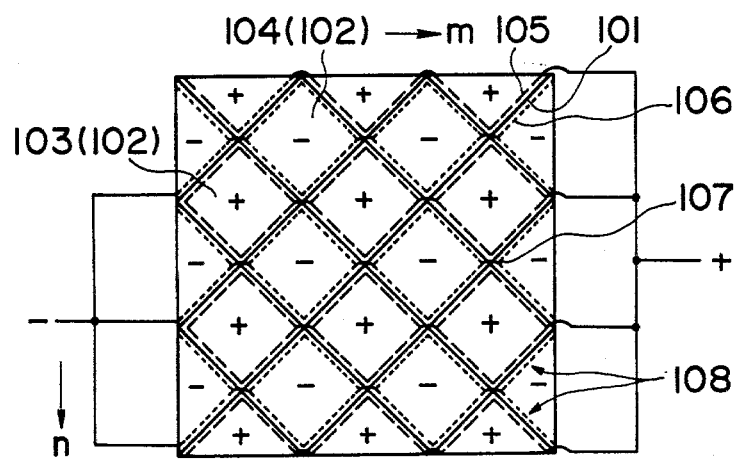
FIG. 12 is a top plan showing still another embodiment of a storage battery of the invention having a honeycomb structure.

Other embodiments of electrode arrangements in accordance with this invention are shown in FIGS. 10 and 12. In these embodiments, (+) and (−) electrode cells are arranged alternately in a zig-zag fashion in the lattice-type honeycomb, and one unit tube makes up one electrode cell and has four unit electrodes. In this case, the unit electrodes in one unit tube are formed continuous to each other. One (+) electrode cell (cathode cell 103) forms four unit cells 8 in total, one between it and each of the four adjacent (−) electrode cells (anode cells 104). These electrodes have an output equivalent to that of four unit cells connected in parallel to each other (i.e., the current is 4 iA, and the voltage is eV).

As shown in FIG. 10, these unit cell electrodes are connected in parallel to each other for each of (+) and (−), and the number of unit electrodes in the transverse direction is m/2 (where m is the number of honeycomb unit tubes arranged transversely), whereby a current of m/2×4i=2 miA is generated from one connecting line. In the longitudinal direction, a (−) electrode is connected to a tape-like end portion 10 of a straight line partitioning wall, a (+) electrode to the next partitioning wall and a (−) electrode to the next partitioning wall, thus connecting them alternately. As a result, n−½ (where n is the number of honeycomb unit tubes in the longitudinal direction) continuous units are obtained. These units can be further connected in series or in parallel or in a combination of these modes, thereby forming one module cell.

The above connection can be formed at the tape-like end portion 110 at the end of the honeycomb as shown in FIG. 11, and, accordingly, even with an extremely thin diaphragm connection can be provided without short circuiting an electrode on the opposite side. (In FIG. 10, the thickness of the diaphragm is enlarged for the sake of convenience, and the connection is shown at its end surface).

Figure 13:
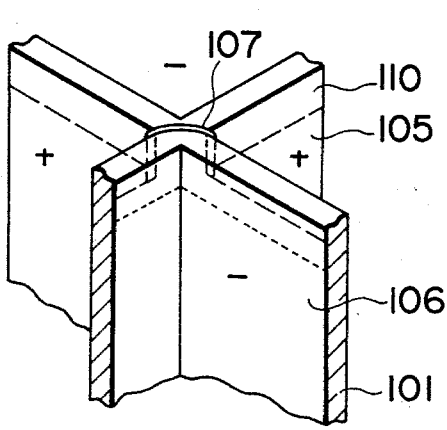
FIG. 13 is an enlarged perspective view of a part of the honeycomb structure shown in FIG. 12.
Figure 15:
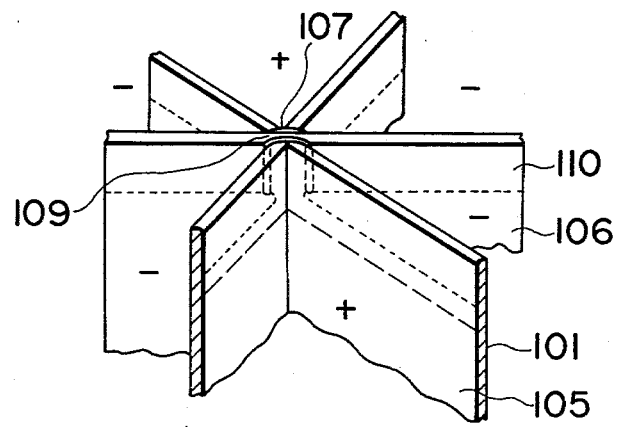
FIG. 15 is an enlarged perspective view of a part of the honeycomb structure shown in FIG. 14.

The following method of connection for such a zig-zag arrangement of positive and negative electrode cells is also feasible. As shown in FIG. 12, two electrode cells of the same polarity which have lattice structure intersection point in common (for example, (+) cells ) are connected so as to form a straight line. The connection at the intersection point of the lattice structure should be formed in such a manner that it does not short circuit with (−) cell electrodes on both sides thereof in the orthogonal direction (FIG. 13). This can be accomplished by the provision of a tape-like end portion 110 as earlier described. In this arrangement, four unit electrodes belonging to one electrode cell are formed continuous to each other. Thus, one transverse row cell unit is formed by one set of positive and negative electrodes in a transverse row. By connecting such cell units in parallel to each other, for example, the entire honeycomb forms one module cell. The output of this cell can be represented by a current of kiA (where K is the number of unit diaphragms, i.e., the number of unit cells, and i is the output current per unit cell) and a voltage of eV (where e is the electromotive force of unit cell). Thus, such a cell provides high current. It is within the scope of the present invention to connect the aforesaid transversely aligned cell units in series and/or in parallel in one module. Further increase of the output voltage can be achieved by connecting a number of such honeycomb module cells in series.

Figure 16:
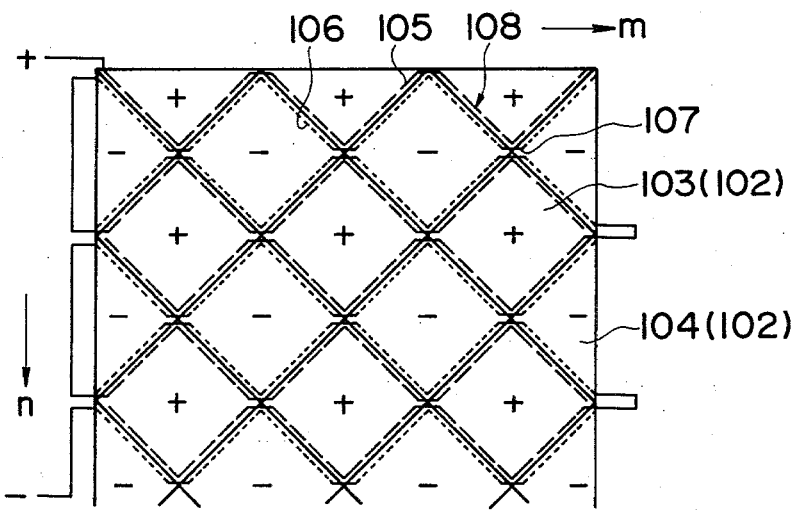
FIG. 16 is a top plan showing still another embodiment of a storage battery of the invention having a honeycomb structure.

In still another embodiment as shown in FIG. 16, which shows a more complicated unit electrode connection, (+) and (−) cells are alternately arranged in zig-zag fashion in the lattice honeycomb, and the (+) electrode cells and the (−) electrode cells are each aligned in a direction connecting the lattice crossings in the transverse direction. Unit electrodes above or below each transverse diagonal line are separately connected in the transverse direction. If desired, insulation may be provided between the connection lines above and below the diagonal line and between two electrodes above the (−) cell and two electrodes below the (−) cell. By connecting (at the lateral end portions) (−) electrodes in one set of transversely aligned cell units thus-formed to (+) electrodes of an adjacent (for example, below in a transverse row) transversely aligned cell units, series connection of transversely aligned cell units within one module becomes possible.

As gases having a high and a low concentration to be passed through solid electrolyte cells as described above, air as a high concentration gas and hydrogen or a hydrocarbon fuel as a low concentration gas can generally be used. Other two types of gases having a difference in the concentration of oxygen can also be used.

Figure 17:
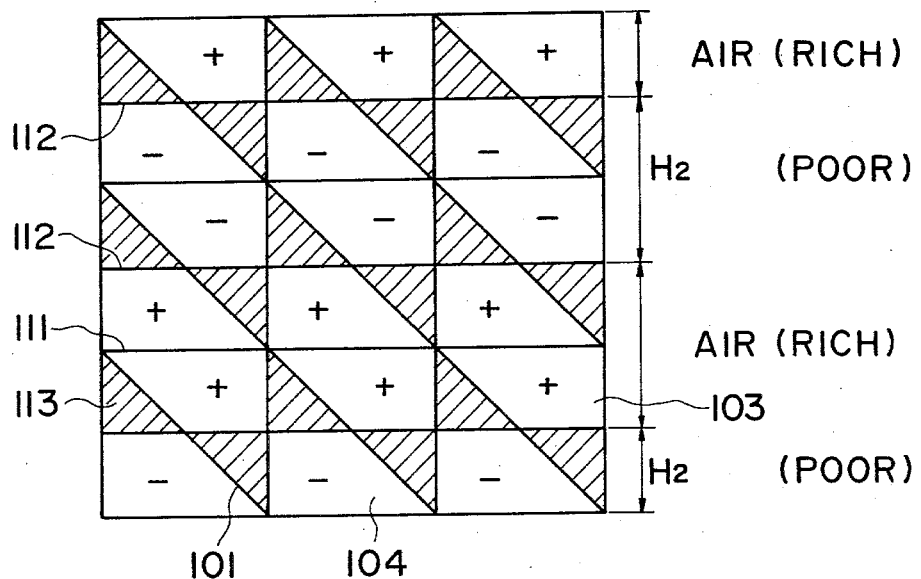
FIGS. 17 and 18 show examples of a gas supplying and discharging device.

According to this invention, two gases having an oxygen pressure difference can be easily supplied to the (+) and (−) electrode cells in the complicated alternate arrangement shown in FIG. 14, if the following method is used: gas supply means having partially closed openings 113 of a triangular shape at the gas supply end, arranged as shown in FIG. 17 are provided, whereby gases are supplied to and discharged from each of the (+) and (−) electrode cells through a laminate-like duct partitioned by partitioning walls 112 which are parallel in the transverse direction.

Figure 18:
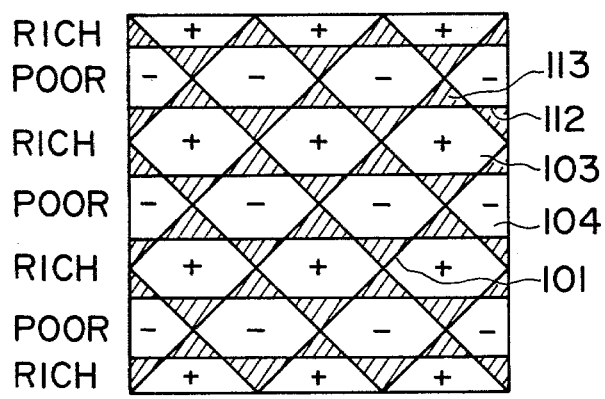

When the (+) and (−) cells are arranged in a zig-zag fashion, gas supply and discharge can be performed by a laminate-like duct having a partially closed portion 113 at the gas supply end having a triangular shape at the gas supply end, as shown in FIG. 18.

Accordingly, as described above, when a voltage exceeding the open circuit voltage is applied to the solid electrolyte cell from an exterior power supply, the system described can immediately serve as an oxygen pump. In this case, the amount of oxygen transported is important, since a large diaphragm area can be easily obtained by the present invention, this constitutes a great advantage with regard to the amount of oxygen transported.

The following non-limiting Examples are given to illustrate the present invention in more detail.

EXAMPLE 1

MgO powder having an average particle diameter of 1 micron (1% by weight) was added to α-alumina powder (99% by weight) having an average particle diameter of 1 micron (maximum particle diameter 3 microns), thereafter being mixed by a ball mill.

To 100 parts by weight of the resulting mixed powder there was added 50 parts by weight of a water-insoluble moisture setting polyurethane resin which serves as an organic binder, the resulting system being kneaded to form a new batch. The details of the water-insoluble moisture setting polyurethane resin is that a polyurethane resin is dissolved in dimethylformamide to form a highly viscous liquid, which is then kneaded with a ceramic powder. Thereafter, when the mixture is brought into contact with water, the dimethylformamide elutes into the water due to its high hydrophilicity, and the polyurethane resin loses the solvent and gelates to be coagulation.

A honeycomb structure was then produced from the raw batch in a customary manner. The resulting honeycomb had an appropriate flexibility but did not deform and lent itself to easy handling. The honeycomb structure was then hardened by natural drying and heated up to 800° C. from ambient in a reducing atmosphere at a rate of 50° C./hour to remove organic matter. Gradually, the reducing atmosphere was replaced by an oxidizing atmosphere, and the honeycomb structure fired at 900° C. for 5 hours therein to oxidize residual carbon and form an unglazed fired body. The reducing atmosphere includes $N_2$ gas or $H_2$ gas or $NH_3$ gas. Alternatively, the reducing atmosphere is provided by air whose amount is 80% or less than that required in the theoretical air-fuel ratio. The oxidizing atmosphere is provided by air whose amount is larger than that required in the theoretical air fuel ratio.

The resulting fired body was embedded in a mixed powder obtained by adding 5% by weight of $Na_2CO_3$ to coarse particles of $\beta$-alumina, the resulting mixed powder of $\beta$-alumina and $Na_2CO_3$ also being packed into the unit tubes of the honeycomb.

In a sheath of magnesia, the honeycomb mixture combination was then heated from ambient at a rate of 100° C./hour to 1,500° C. and maintained at 1,500° C. for 1.5 hours, whereafter the assembly cooled at a rate of 500° C./hour to ambient to provide a honeycomb structure composed of $\beta$-alumina.

A perspective view of the resulting honeycomb structure, after removal of the magnesia sheath, is shown in FIG. 1 wherein reference numeral 1 represents the honeycomb structure, 2 a partitioning wall (web), and 3 a unit tube.

The thickness of the partitioning wall was 0.4 mm. The cross section of each unit tube was a square with each side measuring 9.6 mm (interior dimension), and the exterior shape was a square with one side at the end surface measuring about 100 mm. As a whole, each unit tube constitutes a quadratic prism having a length of 150 mm. The web portions of the honeycomb structure (excluding hollow areas) had a specific gravity of 3.20, and its X-ray diffraction analysis confirmed that it was completely $\beta$-alumina ceramic. The $Na^+$ ion conductivity of the honeycomb structure was found to be 0.05 mho/cm at 300° C., about the same as the prior art. When each partitioning wall (web) is used as a separator, it is small-sized and tough and has high utility as compared with bottomed hollow cylindrical structures or plates as used in the prior art.

When the honeycomb structure is to be produced from a mixture of $\beta''$-$Al_2O_3$ and $\beta$-$Al_2O_3$, the method described in Japanese Patent Application No. 57598/76 filed by the same applicant as the present one is used. Specifically, 87 to 95% by weight of $Al_2O_3$ was mixed with 5 to 13% by weight as $Na_2O$ of a sodium salt, and the mixture was heated at less than 1,500° C. in an oxidizing atmosphere so that the products powder X-ray diffraction pattern exhibited a ratio of the peak intensity $I\beta$ of $\beta$-$Al_2O_3$ at $\alpha=2.69$ Å (017) plane to the peak intensity $I\beta$ of $\beta''$-$Al_2O_3$ at $\alpha=2.60$ Å (01, 11) plane [$I\beta:I\beta''$] within the range of 1.0–0.25. Then, 100 parts by weight of the resulting powder was mixed with less than 3 parts by weight (as oxide) of a monovalent and/or divalent metal ion. Using the resulting product as a raw material, a honeycomb structure was molded and fired in a conventional manner as described earlier in this example. Incidentally, the customary manner of extrusion method for forming thin walled honeycomb structures is disclosed in U.S. Pat. No. 3,790,654.

EXAMPLE 2

The same green honeycomb structure as in Example 1 was molded. Using the same raw batch, a thin sheet of a thickness of 1 mm was extrusion molded in a conventional manner. The thin sheet was adhered closely to one end of the green honeycomb without a gap using an adhesive obtained by adding dimethylformamide to the aforesaid raw batch to reduce its viscosity. The assembly was dried, and thereafter, by the same method as in Example 1, a honeycomb structure of $\beta$-alumina with one end open and the other end closed was produced. The thickness of the partitioning wall was 0.4 mm. The characteristics of the honeycomb structure as a material were the same as those of the honeycomb structure obtained in Example 1, and it could be used as a cationically conductive crystalline solid separator which was small-sized, tough and had high utility.

EXAMPLE 3

The extrusion raw batch as in Example 1 was prepared. Using a part of the raw batch, single layers A of a honeycomb structure including a number of unit tubes 3' in one direction by partitioning walls 2' were produced by the same molding method as in Example 1.

Using another part of the raw batch, corrugated sheets B having a number of bent portions 4 comprising sinusoidal curves in cross section as shown in FIG. 4 were extrusion molded in the same way. The thickness of the partitioning wall was 0.4 mm.

Single layers A and corrugated sheets B were alternately laminated so that the axial lines of the unit tubes crossed the axial lines of the bent portions at right angles. The contact portions were bonded by applying an adhesive obtained by adding dimethylformamide to the above raw batch to reduce its viscosity.

A separately produced sheet formed from yet a further part of the raw batch and having a thickness of 0.5 mm was adhered to the bottom surface of the final corrugated sheet B. The resulting assembly was dried and then fired as in Example 1 to provide a honeycomb structure 1' composed of $\beta$-$Al_2O_3$.

Figure 20:
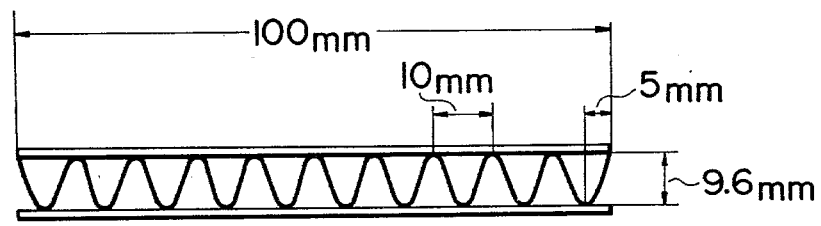
FIG. 20 is a cross-sectional view of a sinusoidal material showing the dimension thereof.

A perspective view of the resulting honeycomb structure is shown in FIG. 2. In this honeycomb structure, the axial lines of the unit tubes in the odd-numbered stages from the top (the first, third, fifth, etc.) are at right angles to those of the unit tubes in the even-numbered stages (the second, fourth, sixth, etc.). The dimension of the sinusoidal curved sheet is shown in FIG. 20. In FIG. 20, transverse length of the corrugated sheet of 100 mm is shown. Please be noted that the longitudinal length thereof is also 100 mm.

EXAMPLE 4

Fine powdered zirconia (91 mol%) and fine powdered yttria (9 mol%) were micropulverized and mixed by a ball mill. The fine powdered zirconia includes 96% of the powders having average particle size of 2.5$\mu$ or less, and the fine powdered yttria includes 58% of the powders having average particle size of 5μ or less. The mixture was extrusion molded as in Example 1, heated first in a reducing atmosphere from ambient to 800° C. at a rate of 100° C./hour, and, while gradually replacing the atmosphere by an oxidizing atmosphere, heated to 1,600° C. at a rate of 100° C./hour. The product was maintained at 1,600° C. for 2 hours and then the temperature lowered at a rate of 100° C./hour to ambient to complete firing.

The density of the fired web, excepting hollow areas, was 5.50 g/cm$^3$, and the product had a volume inherent resistivity at 350° C. of less than 40 kiloohms.cm.

A conventional platinum paste was coated on the webs except for their end surfaces and the resulting assembly baked to form a porous platinum electrode. The thickness of the partitioning wall was 0.1 mm.

When this product is used as an oxygen ion conductive crystalline solid separator, it permits removal of a high voltage or current because its webs are thinner, further, the number of unit tubes can be larger than a conventional assembly of plates or pipes. In addition, it has high strength and is easy to produce, and, as a cell, has good efficiency and a high utility. When used as an oxygen concentration meter, it provides an element having good sensitivity.

EXAMPLE 5

Fine α-alumina powder having an average particle diameter of 1 micron (99% by weight) was mixed with 1% by weight of MgO powder having an average particle diameter.

To 100 parts by weight of the resulting powder was added 50 parts by weight of a water-insoluble, moisture-setting polyurethane resin, and they were kneaded. Using the resulting raw batch, a honeycomb structure was molded by a conventional method.

The honeycomb structure had a moderate degree of flexibility, but did not deform. It was allowed to naturally dry and was then heated from ambient to 800° C. in a reducing atmosphere at a rate of 50° C./hour to remove organic matter. The reducing atmosphere was gradually replaced by an oxidizing atmosphere and it was fired at 900° C. for 5 hours to oxidize residual carbon and to provide an unglazed fired body.

The fired body was embedded in a mixed powder of coarse β-alumina particles and 5% by weight of sodium carbonate (based on the β-alumina) and the mixed powder was filled into the unit tubes of the honeycomb. The honeycomb was then heated from ambient at a rate of 100° C./hour to 1,500° C., maintained at 1,500° C. for 1.5 hours, and then cooled at a rate of 500° C./hour to provide a honeycomb structure of β-alumina.

Figure 9:
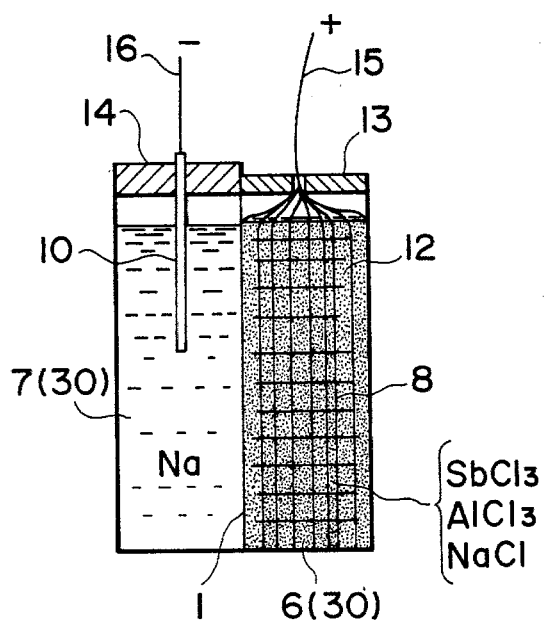
FIG. 9 is a partial sectional view of the storage battery of the invention produced in Example 5 to be later given.

The average thickness of the partitioning walls 1 (webs) of the honeycomb structure was 0.2 mm. Each unit tube had a square cross section had an outside dimension of 5.1 mm and an interior dimension of 4.9 mm in the longitudinal direction, and an outside dimension of 5.1 mm and an inside dimension of 4.9 mm in the transverse direction. The thickness of the partitioning wall was 0.1 mm. Each of the unit tubes was closed at its bottom surface. A honeycomb having 12 unit tubes in both the longitudinal and transverse directions had a size of 6×6×10 (height) cm. Anode cells and cathode cells were alternately disposed (in a zig-zag fashion) in the unit tubes of this honeycomb as shown in FIG. 6. The enlarged sectional view of this arrangement is shown in FIG. 9. Nickel steel was used as cathode 8 and a nickel rod as anode 10. As the anode reactant, a mixture of 279 g of a molten mixed salt containing AlCl$_3$, NaCl and SbCl$_3$ in molar ratio of 51:27:22 with 11% of graphite powder as an auxiliary current collector 12 was placed into the cathode area. In anode 7, molten metallic sodium (161 g) was placed. As a result, the available diaphragm area was 784 cm$^2$.

Operations after filling reactants to prevent oxidation and moisture absorption by the sodium were performed in an atmosphere of dry argon. The top portion of the cathode cell was sealed with a tight stopper 13 of Teflon rubber. The anode was fixed by means of alumina ceramic insulator 14. Electrode lead lines 15, 16 were then connected in parallel as shown in FIG. 6 to form an integrated cell.

Thereafter, a nichrome wire was wrapped around the periphery and bottom surface of the honeycomb structure and the structure covered with a heat insulating material. By passing an electric current therethrough, the molten reactant was maintained at 200° C. In this state, the various measurements shown in Table 1 were performed, with the results obtained being shown in Table 1 in the row headed "No. 1". The honeycomb β-alumina had a specific resistance of 36 ohms.cm (at 200° C.). The degree of alkali ion conductivity which the honeycomb structure shows is 0.029 mho/cm.

CONTROL EXAMPLE NO. 1 R

As a control, a bottomed hollow cylindrical structure of β-alumina having an interior diameter of 15 mm, a length of 150 mm and a thickness of 1 mm was produced in the same way as in Example 5. Anodes and cathodes as used in Example 5 were used. A portion corresponding to anode cell 6 in FIG. 6 was made the outside of the bottomed hollow cylindrical structure, and a portion corresponding to the cathode cell 7 in FIG. 6 was made the inside of the bottomed cylindrical structure. As an exterior container, a Pyrex glass container was used. A conventional storage battery was thus produced. By the same exterior heating and temperature maintenance as in Example 5, the molten reactant was maintained at 200° C. and the various measurements shown in Table 1 were performed. The results are shown in Table 1 in the row headed "No. 1 R". Conditions other than those described above were the same as in Example 5. The size of this electrode cell was 8.5×16×10 (height) cm. The degree of alkali ion conductivity which the honeycomb structure shows is 0.029 mho/cm.

EXAMPLE 6

The same honeycomb as in Example 5 was used with the same electrodes as in Example 5 being provided. The thickness of the partitioning wall was 0.1 mm. A frit having a coefficient of expansion substantially equal to that of β-alumina and good corrosion resistance to sodium was used as the tight sealing stopper. Except for the cathode reactant and the cathode, all other procedures and conditions were as in Example 5. As the cathode reactant, sodium polysulfide composed mainly of Na$_2$S$_5$ was used, and a graphite felt was used as the anode. The various measurements shown in Table 1 were performed while maintaining the temperature at 300° C. The results are shown in Table 1 in the row headed "No. 2". The degree of alkali ion conductivity which the honeycomb structure shows is 0.091 mho/cm.

CONTROL EXAMPLE NO. 2 R

The same honeycomb structure as in Control Example No. 1 R was used except that the cathode reactant and the anode were changed to those used in Example 6 above. The measurements were performed under the same conditions as in Example 6 and the results are shown in Table 1 in the row headed "No. 2R". The degree of alkali ion conductivity which the honeycomb structure shows is 0.091 mho/cm.

EXAMPLE 7

Stabilized zirconia powder containing 9% by weight of $Y_2O_3$ was pulverized by a ball mill to particles at least 95% of which had a particle diameter of less than 2.5 microns.

Using the powder, a honeycomb structure having a partitioning wall thickness of 0.2 mm and a height of 206 mm and consisting of 400 unit tubes (20 in the longitudinal direction and 20 in the transverse direction) each of a square cross section with one side measuring 5 mm was produced in a conventional manner.

The green honeycomb structure thus-obtained was heated from ambient in an oxidizing atmosphere at a rate of 100° C./hour to 1,700° C. and fired at 1,700° C. for 4 hours, whereafter it was cooled at a rate of 100° C./hour to ambient to provide an electrolyte honeycomb structure.

Figure 19:
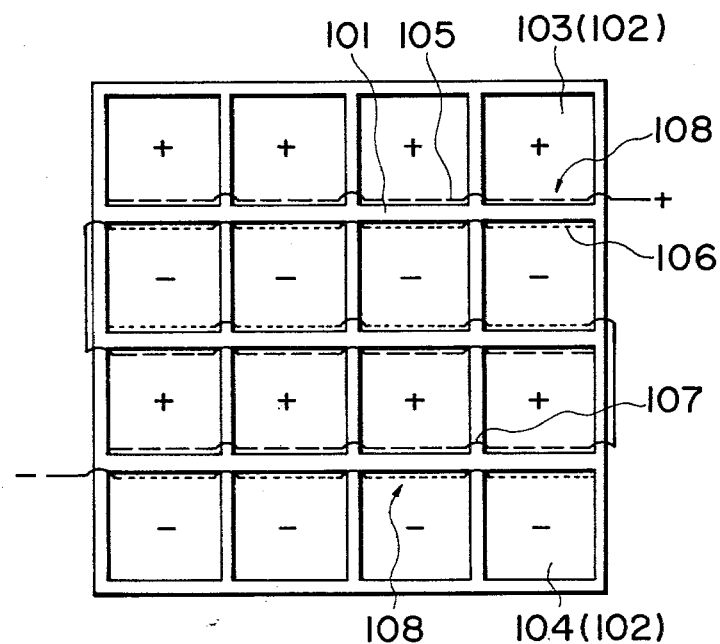
FIG. 19 shows the storage battery of the invention having a honeycomb structure as formed in Example 7.

Wax was coated in tape form on both sides and the top end of the partitioning walls at its both end portions to leave a tape-like end portion with a width of 3 mm. Further, as shown in FIG. 19, wax was coated on vertical partitioning walls, and the structure was dipped in a dilute slurry of a conventional platinum paste with excess paste being blown away by compressed air to dry the same. This step was repeated several times to obtain a paste coating thickness (dry) of about 0.08 mm.

The paste coating was then baked to form an electrode having an available height of 200 mm on both side surfaces of the partitioning wall. As shown in FIG. 19, 20 unit cells comprising such unit electrodes were connected in parallel to each other in the transverse direction to form one cell unit. Nineteen (19) such units were connected in series in the longitudinal direction to provide one honeycomb module cell.

When the cell was operated at 1,000° C. using $H_2$ (−) as a fuel and air (+) as an oxygen source, each unit cell generated an output of 0.71 V terminal voltage×1.2 A current. The module as a whole generated an output of 13.5 V terminal voltage×24 A current.

While the invention has been described in detail and with reference to specific embodiments thereof, it will be apparent to one skilled in the art that various changes and modifications can be made therein without departing from the spirit and scope thereof.

What is claimed is:

1. A storage battery comprising a partitioning membrane, an anolyte consisting of molten sodium metal and a catholyte selected from the group consisting of sodium sulfide and a mixture of antimony chloride, aluminum chloride and sodium chloride, wherein the partitioning membrane has a honeycomb structure formed by a plurality of unit tubes arranged in close configuration, the cross-sectional shape of said unit tubes being polygonal, said partitioning membrane with said honeycomb structure consisting of fluid-impermeable alkali ion-conductive material selected from β-alumina (β-$Al_2O_3$) or β-alumina containing β"-alumina (β"-$Al_2O_3$), and said partitioning membrane with said honeycomb structure providing alternating anode and cathode cells, each separated by said membrane, and thus providing a plurality of unit cells, said unit cells being connected in series or in parallel.

2. A storage battery as claimed in claim 1, wherein said honeycomb partitioning membrane comprises potassium ion conductive β-alumina.

3. A storage battery as claimed in claim 1, wherein said honeycomb partitioning membrane is formed from a mixed powder of 100 parts by weight of β-alumina containing β"-alumina admixed with less than 3 parts by weight, expressed as oxide, of a monovalent metal ion and/or divalent metal ion other than sodium, the intensity ratio Iβ/Iβ" determined with β-alumina as $\alpha = 2.69$ Å (0, 1, 7) and β"-alumina as $\alpha = 2.60$ Å (0.1.11) being in the range of 0.25 to 1.0.

4. A storage battery as claimed in claim 1, wherein sodium is used as the anolyte and sodium sulfide is used as the catholyte.

5. A storage battery as claimed in claim 1, wherein sodium is used as the anolyte and a mixture of antimony chloride, aluminum chloride and sodium chloride is used as the catholyte.

6. A solid electrolytic storage battery comprising an anolyte consisting of molten sodium metal and a catholyte selected from the group consisting of sodium sulfide and a mixture of antimony chloride, aluminum chloride and sodium chloride and partition walls made of an oxygen ion conductive material with a fluid-impermeable and oxygen transmittive electrode disposed on the surface of said partition walls, wherein said partition walls are in the form of honeycomb structure comprising unit tubes characterized by a polygonal cross-section, said partition walls being formed of stabi-

TABLE 1

| Test | Thickness of the Diaphragm (mm) | Internal Resistance (ohms) | Internal Voltage Loss (V) | Voltage (V) | Temperature (°C.) | Reactant | Current Density (mA/Cm²) |
| --- | --- | --- | --- | --- | --- | --- | --- |
| Example 5 (No. 1) Control | 0.2 | 0.135 | 0.24 | 2.52 | 200 | Anode: Na Cathode: $AlCl_3$ NaCl $SbCl_3$ | 20 |
| Example No. 1 R | 1 | 0.51 | 0.89 | 2.43 | 200 | | 20 |
| Example 6 (No. 2) Control | 0.2 | 0.07 | 0.66 | 1.63 | 300 | Anode: Na Cathode: $Na_2S_5$ | 100 |
| Example No. 2 R | 1 | 0.27 | 2.75 | 1.42 | 300 | | 100 | lized zirconia and functioning as partitioning membranes so as to provide an oxygen density differential between neighboring cells, and said partition walls being provided with insulated electrodes at an area other than the upper end portion of said partition walls, and said unit cells being arranged in parallel.

7. A storage battery as claimed in claim 6, wherein said unit cells are connected in series.

8. A storage battery as claimed in claim 6, wherein a single layer of said honeycomb structure comprises partition walls oriented in one direction alternated with a separate honeycomb layer comprising partition walls directed perpendicular to the partition wall of said single layer honeycomb, said two layers forming at least one stacked layer.

9. A storage battery as claimed in claim 6, wherein a unit cell is provided between neighboring electrode cells arranged alternately in a zig-zag fashion.

* * * * *